United States Patent [19]

Seitz et al.

[11] Patent Number: 5,504,109
[45] Date of Patent: Apr. 2, 1996

[54] SUSBSTITUTED AMINO ACID AMIDE DERIVATIVES THEIR PREPARATION AND USE

[75] Inventors: Thomas Seitz; Heinz-Wilhelm Dehne, both of Monheim, Germany

[73] Assignee: Bayer Aktiengesellschaft, Leverkusen, Germany

[21] Appl. No.: 975,755

[22] Filed: Nov. 13, 1992

Related U.S. Application Data

[63] Continuation of Ser. No. 786,489, Nov. 1, 1991, abandoned, and a continuation-in-part of Ser. No. 514,919, Apr. 25, 1990, Pat. No. 5,210,084.

[30] Foreign Application Priority Data

Nov. 10, 1990 [DE] Germany .......................... 40 35 851.8

[51] Int. Cl.$^6$ ..................................................... A61K 31/27
[52] U.S. Cl. ........................... 514/484; 514/346; 514/352; 514/476; 514/480
[58] Field of Search ..................................... 560/115, 159; 546/335, 292; 564/193; 514/480, 484, 346, 352, 476

[56] References Cited

U.S. PATENT DOCUMENTS

| 4,559,083 | 12/1985 | Balough et al. | 558/240 X |
| 4,944,796 | 7/1990 | Wee | 558/240 X |
| 5,210,084 | 5/1993 | Wollweber et al. | 514/237.5 |

FOREIGN PATENT DOCUMENTS 450355 10/1991 European Pat. Off. .

*Primary Examiner*—Allen J. Robinson
*Assistant Examiner*—Brian M. Burn
*Attorney, Agent, or Firm*—William C. Gerstenzang; Sprung Horn Kramer & Woods

[57] ABSTRACT

Amino-acid derivatives of the formula

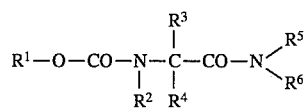

in which $R^1$ represents alkyl, alkenyl, alkinyl, halogenoalkyl, halogenoalkenyl, halogenoalkinyl, cycloalkyl, cycloalkenyl, unsubstituted or substituted aryl, unsubstituted or substituted aralkyl, unsubstituted or substituted heteroaryl, and unsubstituted or substituted heteroarylalkyl, $R^2$, $R^5$ are identical or different and represent hydrogen or lower alkyl, $R^3$, $R^4$ represent hydrogen, cycloalkyl or alkyl, or $R^3$ and $R^4$, together with the carbon atom to which they are bonded, form a cycloalkyl ring, $R^6$ represents unsubstituted or substituted straight-chain or branched cycloalkylalkyl, unsubstituted or substituted straight-chain or branched cycloalkenyl, alkyl, or alkyl-bridged cycloalkylalkyl.

The compounds are useful as pesticidal agents.

10 Claims, No Drawings

SUBSTITUTED AMINO ACID AMIDE DERIVATIVES THEIR PREPARATION AND USE

This is a continuation of application Ser. No. 786,489, filed Nov. 1, 1991, now abandoned, and a continuation-in-part of application Ser. No. 07/514,919, filed Apr. 25, 1990, now U.S. Pat. No. 5,210,084.

The present invention relates to novel substituted amino acid amide derivatives and a plurality of processes for their preparation, as well as to their use in pesticides.

The substances according to the invention have an excellent action when used for combating pests. In particular, the substances according to the invention can be used as fungicides, mainly in plant protection.

Certain amino acid amides have already been disclosed, such as, for example, N-tert.-butoxycarbonyl-L-leucyl-benzyl-amide (EP-A-236,874).

However, the use of these compounds in pesticides is not described.

The present application therefore relates to novel amino acid amide derivatives of the general formula (I)

$$R^1-O-CO-N(R^2)-C(R^3)(R^4)-CO-N(R^5)(R^6) \quad (I)$$

in which $R^1$ represents alkyl, alkenyl, alkinyl, halogenoalkyl, halogenoalkenyl, halogenoalkinyl, cycloalkyl, cycloalkenyl, unsubstituted or substituted aryl, unsubstituted or substituted aralkyl, unsubstituted or substituted heteroaryl and unsubstituted or substituted heteroarylalkyl, $R^2$, $R^5$ are identical or different and represent hydrogen or lower alkyl, $R^3$, $R^4$ represent hydrogen, cycloalkyl or alkyl or $R^3$ and $R^4$ together with the carbon atom to which they are bonded form a cycloalkyl ring, $R^6$ represents unsubstituted or substituted straight-chain or branched cycloalkylalkyl, unsubstituted or substituted straight-chain or branched cycloalkenyl, -alkyl or alkyl-bridged cycloalkylalkyl.

Moreover, the compounds of the formula (I) can contain one or more chiral centres and can therefore exist in various mixtures of enantiomers and diastereomers which, if appropriate, can be resolved in the customary fashion. The invention claims the pure enantiomers and diastereomers as well as the mixtures.

For the sake of simplicity, the following text will always mention compounds of the formula (I), even though this is understood as meaning the pure compounds as well as the mixtures with various proportions of isomeric, enantiomeric and diastereomeric compounds.

Formula (I) provides a general definition of the amino acid amide derivatives which are substituted according to the invention.

Unless otherwise defined, the preferred meanings in the following general formulae are:

Alkyl, on its own or in compound radicals—straight-chain or branched alkyl having 1 to 6, in particular 1 to 4, carbon atoms. The following may be mentioned by way of example and as preferred: methyl, ethyl, n- and i-propyl, n-, i-, s- and t-butyl.

Alkenyl—straight-chain or branched alkenyl having 2 to 6, in particular 2 to 4, carbon atoms. The following may be mentioned by way of example and as preferred: optionally substituted ethenyl, 1-propenyl, 2-propenyl and 3-butenyl.

Alkinyl—straight-chain or branched alkinyl having 2 to 6, in particular 2 to 4, carbon atoms. The following may be mentioned by way of example and as preferred: optionally substituted ethinyl, 1-propinyl, 2-propinyl and 3-butinyl.

Halogenoalkyl—straight-chain or branched halogenoalkyl having 1 to 6, in particular 1 to 4, carbon atoms and 1 to 9, in particular 1 to 5, and especially 1 to 3, identical or different halogen atoms such as fluorine, chlorine, bromine, iodine, in particular fluorine and chlorine. The following may be mentioned by way of example and as preferred: fluoromethyl, fluoroethyl, fluoropropyl, chloropropyl, fluorobutyl, chlorobutyl, difluoromethyl, difluoroethyl, dichloroethyl, difluoropropyl, dichloropropyl, difluorobutyl, dichlorobutyl, trifluoromethyl, trichloromethyl, trifluoroethyl, trichloroethyl, trifluoropropyl, trichloropropyl, trifluorobutyl and trichlorobutyl.

Halogenoalkenyl and halogenoalkinyl—straight-chain or branched optionally substituted halogenoalkenyl, or halogenoalkinyl, having 2 to 6, in particular 2 to 4, carbon atoms and 1 to 9, in particular 1 to 5, and especially 1 to 3, identical or different halogen atoms such as fluorine, chlorine, bromine, iodine, in particular fluorine and chlorine. The following may be mentioned by way of example and as preferred: fluoroallyl, chloroallyl, fluorobutenyl, chlorobutenyl, fluoropropargyl, chloropropargyl, fluorobutinyl and chlorobutinyl.

Cycloalkyl—represents a 3- to 7-membered substituted or unsubstituted ring, in particular a ring having 3, 5 or 6 carbon atoms. The following may be mentioned by way of example and as preferred: cyclopropyl, cyclobutyl, cyclopentyl, cyclohexyl and cycloheptyl.

Cycloalkenyl—substituted or unsubstituted cycloalkenyl having 3 to 7, in particular 3 to 6, carbon atoms and 1 or 2 double bonds.

Aryl—unsubstituted or substituted aryl having 6 to 10 carbon atoms. The following may be mentioned by way of example and as preferred: in each case unsubstituted or substituted phenyl and naphthyl, in particular unsubstituted or substituted phenyl.

Aralkyl— unsubstituted or substituted aralkyl having 1 to 4, in particular 1 or 2, carbon atoms in the straight-chain or branched alkyl moiety and 6 to 10 carbon atoms, preferably phenyl, in the aryl moiety. The following may be mentioned by way of example and as preferred: benzyl, 1,1- and 1,2-phenethyl and 1,1-, 1,2-, 1,3- and 2,2-phenylpropyl.

Heteroaryl—unsubstituted or substituted 5- to 9-membered ring, in particular 5- to 7-membered ring, which contains 1 to 4, preferably 1 to 3, identical or different hetero atoms. Hetero atoms which may preferably be mentioned are oxygen, sulphur and nitrogen. The following may be mentioned by way of example and as preferred: pyrimidinyl, thienyl, furyl, pyrazinyl, thiazolyl and, in particular, pyridyl.

Heteroarylalkyl—the heteroaryl moiety corresponds to the abovementioned definitions and preferred ranges. The alkyl moiety is straight-chain or branched and contains 1 to 4, in particular 1 or 2, carbon atoms. The following may be mentioned by way of example and as preferred: heteroarylmethyl, 1,1- and 1,2-heteroarylethyl.

The optionally substituted radicals of the general formulae can carry one or more, preferably 1 to 3, in particular 1 or 2, identical or different substituents. The following substituents may be mentioned by way of example and as preferred: alkyl having preferably 1 to 4, in particular 1 or 2, carbon atoms such as methyl, ethyl, n- and i-propyl and n-, i-, sec- and t-butyl; alkoxy having preferably 1 to 4, in particular 1 or 2, carbon atoms such as methoxy, ethoxy, n- and i-propyloxy and n-, i-, sec- and t-butyloxy; alkylthio having preferably 1 to 4, in particular 1 or 2, carbon atoms such as methylthio, ethylthio, n- and i-propylthio and n-, i-, sec- and t-butylthio; halogenoalkyl, halogenoalkoxy and halogenoalkylthio having preferably 1 to 4, in particular 1 or 2, carbon atoms and preferably 1 to 9, in particular 1 to 5, halogen atoms, the halogen atoms being identical or different and preferably representing fluorine, chlorine or bromine, in particular fluorine, such as trifluoromethyl, difluoromethyl, pentafluoroethyl, tetrafluoroethyl, trifluorochloroethyl, trifluoroethyl, trifluoroethoxy, difluoromethoxy, pentafluoroethoxy, tetrafluoroethoxy, trifluorochloroethoxy, trifluoromethoxy and trifluoromethylthio; halogen, preferably fluorine, chlorine, bromine and iodine, in particular fluorine, chlorine and bromine; alkylalkoxy having 1 to 4, in particular 1 or 2, carbon atoms in each alkyl moiety; carbonylalkoxy having 1 to 4, in particular 1 or 2, carbon atoms in the alkyl moiety, such as carbonylmethoxy and carbonylethoxy.

The definitions listed here analogously also apply to the definitions in the following preferred combinations of radicals.

Preferred compounds of the formula (I) are those in which $R^1$ represents straight-chain or branched alkyl having 1 to 6 carbon atoms, straight-chain or branched alkenyl or alkinyl having 2 to 6 carbon atoms, straight-chain or branched halogenoalkyl having 1 to 6 carbon atoms and 1 to 9 identical or different halogen atoms, straight-chain or branched halogenoalkenyl or halogenoalkinyl having 2 to 6 carbon atoms and 1 to 9 identical or different halogen atoms or substituted or unsubstituted cycloalkyl or cycloalkenyl having 3 to 7 carbon atoms, or represents in each case unsubstituted or substituted phenyl and pyridyl, or phenylalkyl which has 1 to 4 carbon atoms in the straight-chain or branched alkyl moiety and which is unsubstituted or substituted in the phenyl moiety, suitable substituents in the pyridyl or phenyl moiety in each case being: alkyl, alkoxy and alkylthio, in each case having 1 to 4 carbon atoms; halogenoalkyl, halogenoalkoxy and halogenoalkylthio, in each case having 1 to 4 carbon atoms and 1 to 9 halogen atoms, the halogen atoms being identical or different; halogen; alkylalkoxy having 1 to 4 carbon atoms in each alkyl moiety; carbonylalkoxy having 1 to 4 carbon atoms in the alkyl moiety;

$R^2$ and $R^5$ represent hydrogen or methyl, $R^3$ and $R^4$ are identical or different and represent hydrogen, unsubstituted or substituted cycloalkyl having 3 to 7 carbon atoms or straight-chain or branched alkyl having 1 to 6 carbon atoms, or $R^3$ and $R^4$ together with the carbon atom to which they are bonded form a cycloalkyl ring having 3 to 7 carbon atoms, and $R^6$ represents unsubstituted or substituted cycloalkylalkyl having 3 to 7 carbon atoms in the cycloalkyl moiety and 1 to 6 carbon atoms in the straight-chain or branched alkyl moiety, or represents unsubstituted or substituted cycloalkenylalkyl having 5 to 8 carbon atoms in the cycloalkenyl moiety and 1 to 6 carbon atoms in the straight-chain or branched alkyl moiety, or represents cycloalkylalkyl which has 5 to 8 carbon atoms in the cycloalkyl moiety, which is unsubstituted or substituted and which is bridged by alkyl, having 1 to 4 carbon atoms in the bridging alkyl moiety and 1 to 6 carbon atoms in the straight-chain or branched alkyl moiety, suitable substituents being: alkyl, alkoxy and alkylthio, in each case having 1 to 4 carbon atoms; halogenoalkyl, halogenoalkoxy and halogenoalkylthio, in each case having 1 to 4 carbon atoms and 1 to 9 halogen atoms, the halogen atoms being identical or different; hydroxyl; dialkylamino having 1 to 4 carbon atoms per alkyl group; alkylalkoxy having 1 to 4 carbon atoms in each alkyl moiety.

Particularly preferred compounds of the formula (I) are those in which $R^1$ represents straight-chain or branched alkyl having 1 to 4 carbon atoms, straight-chain or branched alkenyl or alkinyl having 2 to 4 carbon atoms, straight-chain or branched halogenoalkyl having 1 to 4 carbon atoms and 1 to 5 identical or different halogen atoms, straight-chain or branched halogenoalkenyl or halogenoalkinyl having 2 to 4 carbon atoms and 1 to 5 identical or different halogen atoms or unsubstituted or substituted cycloalkyl or cycloalkenyl having 3 to 6 carbon atoms, and furthermore represents phenyl which is unsubstituted or monosubstituted to trisubstituted by identical or different substituents, suitable substituents being the following: alkyl, alkoxy and alkylthio, in each case having 1 to 4 carbon atoms; halogenoalkyl, halogenoalkoxy and halogenoalkylthio having 1 or 2 carbon atoms and 1 to 5 halogen atoms, the halogen atoms being identical or different; fluorine, chlorine, bromine and iodine; alkylalkoxy having 1 to 2 carbon atoms in each alkyl moiety; carbonylalkoky having 1 or 2 carbon atoms in the alkyl moiety;

$R^2$ and $R^5$ represent hydrogen, $R^3$ and $R^4$ are identical or different and represent hydrogen unsubstituted or substituted cycloalkyl having 3 to 6 carbon atoms or straight-chain or branched alkyl having 1 to 5 carbon atoms, or $R^3$ and $R^4$ together with the carbon atom to which they are bonded form a cycloalkyl ring having 3 to 6 carbon atoms and $R^6$ represents unsubstituted or substituted cycloalkylalkyl having 3 to 6 carbon atoms in the cycloalkyl moiety and 1 to 4 carbon atoms in the straight-chain or branched alkyl moiety, or represents unsubstituted or substituted cycloalkenylalkyl having 5 to 7 carbon atoms in the cycloalkenyl moiety and 1 to 4 carbon atoms in the straight-chain or branched alkyl moiety, or represents cycloalkylalkyl which has 5 to 7 carbon atoms in the cycloalkyl moiety, which is unsubstituted or substituted and which is bridged by alkyl, having 1 to 3 carbon atoms in the bridging alkyl moiety and 1 to 4 carbon atoms in the straight-chain or branched alkyl moiety, suitable substituents being: alkyl, alkoxy and alkylthio, in each case having 1 to 4 carbon atoms; halogenoalkyl, halogenoalkoxy and halogenoalkylthio having 1 to 2 carbon atoms and 1 to 5 halogen atoms, the halogen atoms being identical or different; hydroxyl; dialkylamino having 1 to 2 carbon atoms per alkyl group; alkylalkoxy having 1 to 2 carbon atoms in each alkyl moiety.

Very particularly preferred are those compounds of the formula (I) in which $R^1$ represents methyl, ethyl, n- and i-propyl, n-, i-, s- and t-butyl, fluoromethyl, fluoroethyl, fluoropropyl, chloropropyl, fluorobutyl, chlorobutyl, difluoromethyl, difluoropropyl, dichloropropyl, difluorobutyl, dichlorobutyl, trifluoromethyl, trichloromethyl, trifluoroethyl, trichloroethyl, trifluoropropyl, trichloropropyl, trifluorobutyl, trichlorobutyl, allyl, butenyl, propargyl, butinyl, fluoro or chloroallyl, -butenyl, -propargyl, -butinyl, cyclopropyl, cyclopentyl, cyclohexyl, cyclopentenyl or cyclohexenyl, or represents phenyl which is unsubstituted or monosubstituted to disubstituted by identical or different substituents, suitable substituents being the following: methyl, ethyl, n- and i-propyl, n-, i-, s- and t-butyl, methoxy, ethoxy, i- and n-propoxy, n-, i-, s- and t-butoxy, trifluoromethyl, difluoromethyl, pentafluoroethyl, tetrafluoroethyl, trifluorochloroethyl, trifluoroethyl, trifluoroethoxy, difluoromethoxy, pentafluoroethoxy, tetrafluoroethoxy, trifluorochloroethoxy, trifluoromethoxy and trifluoromethylthio; chlorine, bromine, fluorine, and $R^2$ and $R^5$ represent hydrogen and $R^3$ and $R^4$ are identical or different and represent hydrogen, methyl, ethyl, n- or i-propyl, n-, i-, s- or t-butyl, 3-pentyl, cyclopropyl, cyclopentyl or cyclohexyl or $R^3$ and $R^4$ together with the carbon atom to which they are bonded form a cyclopropyl, cyclopentyl or cyclohexyl ring or, in particular, $R^3$ represents i-propyl, s-butyl or cyclopentyl and $R^4$ represents hydrogen, $R^6$ represents unsubstituted or substituted cycloalkylalkyl having 3, 5 or 6 carbon atoms in the cycloalkyl moiety and 1 to 3 carbon atoms in the straight-chain or branched alkyl moiety, or represents unsubstituted or substituted cycloalkenylalkyl having 5 to 7 carbon atoms in the cycloalkenyl moiety and 1 to 3 carbon atoms in the straight-chain or branched alkyl moiety, or represents unsubstituted or substituted cycloalkylalkyl which is bridged by alkyl and which has 5 to 7 carbon atoms in the cycloalkyl moiety, having 1 to 2 carbon atoms in the bridging alkyl moiety and 1 to 3 carbon atoms in the straight-chain or branched alkyl moiety, suitable substituents being the following: methyl, ethyl, n- and i-propyl, n-, i-, s-and t-butyl, methoxy, ethoxy, i- and n-propoxy, n-, i-, s- and t-butoxy, trifluormethyl, difluoromethyl, pentafluoroethyl, tetrafluoroethyl, trifluorochloroethyl, trifluoroethyl, trifluoroethoxy, difluoromethoxy, pentafluoroethoxy, tetrafluoroethoxy, trifluorochloroethoxy, trifluoromethoxy and trifluoromethylthio, hydroxyl, methylthio, ethylthio, n- and i-propylthio, dimethylamino, diethylamino.

The substituted amino acid amide derivatives of the general formula (I)

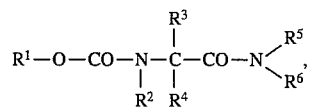

in which $R^1$, $R^2$, $R^3$, $R^4$, $R^5$ and $R^6$ have the abovementioned meaning are obtained when A) a substituted amino acid of the formula (II)

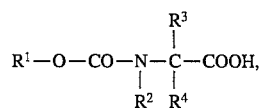

in which $R^1$, $R^2$, $R^3$ and $R^4$ have the abovementioned meaning, or their carboxyl-activated derivatives, is reacted with an amine of the formula (III)

in which $R^5$ and $R^6$ have the abovementioned meaning, if appropriate in the presence of a catalyst, if appropriate in the presence of an acid-binding agent and if appropriate in the presence of a diluent, or B) substituted amino acid amide derivatives of the formula (IV)

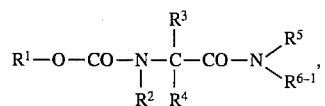

in which $R^1$, $R^2$, $R^3$, $R^4$ and $R^5$ have the abovementioned meaning and $R^{6-1}$ represents unsubstituted or substituted phenyl, suitable phenyl substituents being the substituents mentioned above for $R^6$, are hydrogenated in the presence of a catalyst, if appropriate in the presence of an inert gas and in the presence of hydrogen, if appropriate in the presence of a diluent and if appropriate under pressure.

If, for example, tert.-butoxycarbonyl-D/L-valine and 1-cyclohexylethylamine are used, the course of process A according to the invention can be outlined by the following equation:

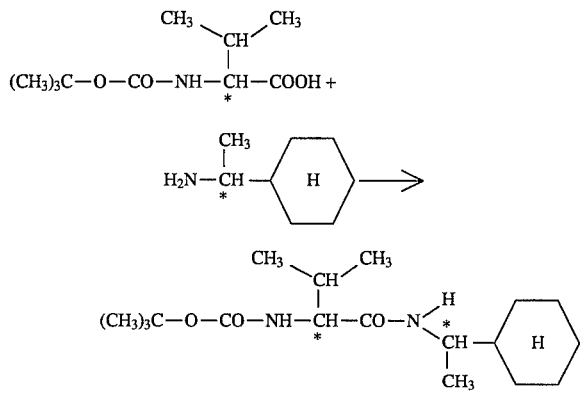

If, for example, N-(i-propyloxy-carbonyl)-L-valine—phenylethylamide and hydrogen are used, with rhodium as the catalyst, the course of process B according to the invention can be outlined by the following equation:

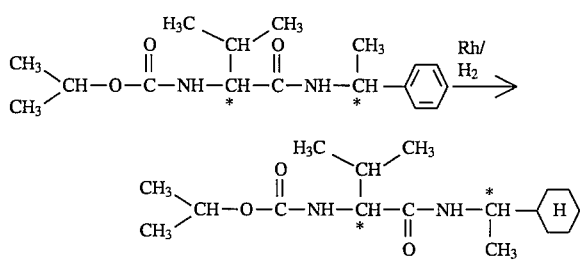

Formula (II) provides a general definition of the amino acid derivatives to be used as starting substances for carrying out process (A) according to the invention. In this formula, $R^1$, $R^2$, $R^3$ and $R^4$ preferably have the meanings which have already been mentioned in connection with the description of the substances of the formula (I) according to the invention as being preferred for these substituents.

The amino acid derivatives of the formula (II) are generally known (cf., for example, Houben-Weyl, Methoden der organischen Chemie [Methods in Organic Chemistry], Volume XV, part 1 and 2, pages 46 et seq. and 112 et seq., Georg Thieme Verlag, Stuttgart 1974; D. Keller et al., Org. Synth. 60, 2145 (1981)] or R. C. Sheppard, A Specialist Periodical Report, Amino-acids, Petides and Proteins, The Royal Society of Chemistry, Burlington House, London 1978, or I. P. Greenstein and M. Winitz, Chemistry of Amino Acids, I. Wiley Sons Inc., New York, London 1961; or E. Schröder and K. Lübke, The Peptides Vol. I, Academic Press, New York, London 1965) or can be obtained by the processes given therein.

The carboxyl-activated derivatives of the amino acid of the formula (II), which are furthermore to be used as starting substances for carrying out the process according to the invention, are generally known.

Suitable carboxyl-activated derivatives of the amino acids of the formula (II) are all carboxyl-activated derivatives, such as acid halides such as, for example, acid chlorides, acid azides, furthermore symmetric and mixed anhydrides such as, for example, the mixed O-alkylcarbonic anhydrides, furthermore activated esters such as, for example, p-nitrophenyl esters or N-hydroxysuccinimide esters, as well as activated forms of the amino acids which have been prepared in situ with condensing agents such as, for example, dicyclohexylcarbodiimide or carbonyldiimidazole.

Substances which are preferably employed are the acid chlorides and mixed anhydrides corresponding to the amino acids of the formula (II). They can be prepared by reacting the amino acids of the formula (II) or their salts in a generally customary fashion with a halogenating agent or one of the generally known agents for preparing mixed arthydrides such as, for example, phosphorus pentachloride, thionyl chloride, oxalyl chloride or isobutyl chloroformate. The use of isobutyl chloroformate is preferred.

The reaction can be carried out in the presence of indifferent diluents such as, for example, aromatic, non-aromatic or halogenated hydrocarbons such as: ketones, such as, for example, acetone; esters such as, for example, ethyl acetate; amides such as, for example, dimethylformamide, nitriles such as, for example, acetonitrile, chlorohydrocarbons such as, for example, methylene chloride, hydrocarbons such as, for example, toluene; or ethers such as, for example, tetrahydrofuran, or mixtures of these, and/or in the presence of an acid-binding agent such as, preferably, a tertiary amine such as, for example, triethylamine, pyridine or N-methylpiperidine, at temperatures of from −78° C. to 100° C., preferably −60° C. to 25° C.

Formula (III) provides a general definition of the amines furthermore to be used as starting substances for carrying out the process according to the invention. In these formulae, $R^1$, Ar', $R^5$ and $R^6$ have the abovementioned meanings.

The amines of the formula (III) are generally known compounds of organic chemistry.

Suitable diluents for process (A) according to the invention are inert, organic solvents such as: ketones, such as acetone or ethyl methyl ketone; esters such as ethyl acetate or methyl acetate; amides such as dimethylformamide; nitriles such as acetonitrile, chlorohydrocarbons such as methylene chloride or carbon tetrachloride; hydrocarbons such as toluene, or ethers, such as tetrahydrofuran, and also, if appropriate, water, and mixtures of these.

Suitable acid-binding agents for the process according to the invention are customary inorganic and organic acid binders. These preferably include tertiary amines such as triethylamine, pyridine or N-methylpiperidine, and also inorganic bases, for example metal hydroxides such as sodium hydroxide and potassium hydroxide, or metal carbonates such as sodium carbonate or calcium carbonate.

If appropriate, process (A) according to the invention is carried out in the presence of a catalyst. The following may be mentioned by way of example: 4-dimethylaminopyridine, 1-hydroxybenzotriazole or dimethylformamide.

When carrying out process (A), the temperatures can be varied within a substantial range. In general, the process is carried out at −78° to +120° C., preferably at −60° to +40° C.

When carrying out process (A) according to the invention, it is preferred to use equimolar amounts.

In this context, the amino acid derivatives of the formula (II) are employed as pure optical isomers (D or L form) or as racemates.

Formula (IV) provides a general definition of the amino acid amide derivatives to be used as starting substances for carrying out process (B) according to the invention. In this formula, $R^1$, $R^2$, $R^3$, $R^4$, $R^5$ and $R^{6-1}$ preferably have the meanings which have already been mentioned for these substituents in connection with the description of the substances of the formula (I) according to the invention.

The substituted amino acid amide derivatives of the formula (IV) are novel and the subject of a patent application, of the applicant company, which does not belong to the published state of the art (cf. the German Patent Applications P 4,026,966, P 3,936,298 and P 3,915,755).

The novel amino acid amide derivatives of the formula (IV) are obtained for example by reacting substituted amino acids of the formula (V)

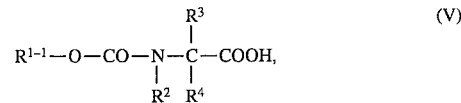

in which
$R^2$, $R^3$ and $R^4$ have the abovementioned meaning and
$R^{1-1}$ represents alkyl and cycloalkyl, or their carboxyl-activated derivatives,
with amines of the formula (VI)

in which
$R^5$ has the abovementioned meaning and
$R^{6-1}$ represents unsubstituted or substituted phenyl, suitable phenyl substituents being the substituents mentioned above for $R^6$, in dichloromethane, in the presence of, for example, N-methylpiperidine as acid-binding agent and isobutyl chloroformate, at temperatures between −60° C. and −10° C.

The formic acids of the formula (V) and the amines of the formula (IV) are generally known compounds of organic chemistry.

Suitable diluents for process B according to the invention are inert, organic solvents, for example alcohols, such as ethanol, isopropanol or s-butanol; saturated hydrocarbons such as n-hexane or cyclohexane.

When carrying out process (B) according to the invention, the temperatures can be varied within a substantial range. In general, the process is carried out at 50° to 250° C., preferably at 0° to 200° C.

Process (B) for the preparation of the novel amino acid amide derivatives of the formula (I) is generally carried out under increased pressure. In general, the process is carried out at a pressure of from 50 to 250 bar, preferably at a pressure of from 100 to 200 bar.

However, under certain conditions, the process can also be carried out under atmospheric pressure or reduced pressure.

Suitable inert gases for this purpose are nitrogen as well as virtually all noble gases, in particular argon.

For carrying out process (B) according to the invention, 0.001 to 1 mole, preferably 0.005 to 0.5 mole, of catalyst are generally employed per mole of the substituted amino acid amide derivative of the formula (IV).

Process (B) according to the invention is carried out under the catalysts customary for reactions of this type. Catalysts which are preferably used are the metals and/or salts or complexes of metals of subgroup VIII of the Periodic System of the Elements; particular mention must be made of ruthenium, rhodium, palladium and platinum.

The invention embraces the pure isomers as well as the mixtures. These mixtures can be separated to give the components by customary methods, for example selective crystallisation from suitable solvents or chromatography on silica gel or aluminium oxide. Racemates can be resolved into the individual enantiomers by customary methods, for example by salt formation with optically active acids such as champhersulphonic acid or dibenzoyltartaric acid and selective crystallisation, or by derivatisation using suitable optically active reagents, resolution of the diastereomeric derivatives and back conversion or resolution on optically active column material.

The active compounds of the formula (I) according to the invention have a powerful action against pests and can be employed in practice for combating undesired harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudo-peronospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago* nuda or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, Alternaria brassicae and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success protectively for combating Phytophthora species on tomatoes or Plasmopara species on grapevines.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogen hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

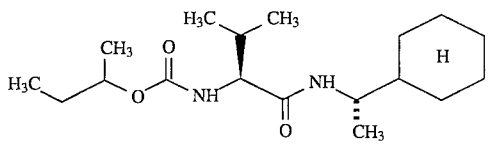

In an autoclave, 3.2 g (10 mmol) of $N^2$-sec.-butyloxycarbonyl-$N^1$-(S(-)-1-phenylethyl)-L-valinamide are dissolved in 50 ml of sec-butanol, and 0.5 g of rhodium-black are added as the catalyst. The mixture is hydrogenated for 12 hours at a hydrogen pressure of 150 bar and a temperature of 150° C. For working up, the catalyst is filtered off, and the filtrate is freed from the solvent in vacuo. For purification, the residue is stirred once with diisopropyl ether. 2.93 g (90% of theory) of colourless $N^2$-sec.-butyloxycarbonyl-$N^1$-(S(+)-1-cyclohexylethyl)-L-valinamide having a melting point of 186° C. are obtained.

The following compounds of the formula (I) are obtained analogously to Example 1:

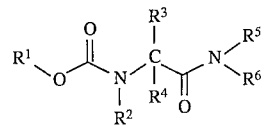

TABLE 1

| No. | $R^1$ | $R^2$ | $R^3$ | $R^4$ | $R^5$ | $R^6$ | Physical constant |
|---|---|---|---|---|---|---|---|
| 2 | —CH(CH$_3$)—CH$_2$CH$_3$ | H | —CH(CH$_3$)$_2$ | H | H | —CH(CH$_3$)—⬡ | mp.: 186° C. |
| 3 | —⬡ | H | —CH(CH$_3$)$_2$ | H | H | —CH(CH$_3$)—⬡ | mp.: 146–147° C. |
| 4 | —CH(CH$_3$)$_2$ | H | —CH(CH$_3$)$_2$ | H | H | —CH(CH$_3$)—⬡ | mp.: 190° C. |
| 5 | —CH(CH$_3$)—CH$_2$CH$_3$ | H | —CH(CH$_3$)$_2$ | H | H | —CH(CH$_3$)—⬡ | mp.: 178° C. (R–)-amine |
| 6 | —CH(CH$_3$)$_2$ | H | —CH(CH$_3$)$_2$ | H | H | —CH(CH$_3$)—⬡—CH$_3$ | mp.: 111° C. |
| 7 | —CH(CH$_3$)$_2$ | H | —CH(CH$_3$)$_2$ | H | H | —CH(CH$_3$)—⬡ | mp.: 165° C. (R–)-amine |
| 8 | —CH(CH$_3$)$_2$ | H | —CH(CH$_3$)$_2$ | H | H | —CH(CH$_3$)—⬡ | mp.: 145° C. |

TABLE 1-continued

| No. | R¹ | R² | R³ | R⁴ | R⁵ | R⁶ | Physical constant |
|---|---|---|---|---|---|---|---|
| 9 | —CH(CH₃)₂ | H | —CH(CH₃)₂ | H | H | 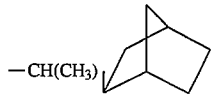 | mp.: 123° C. |
| 10 | —CH(CH₃)—CH₂CH₃ | H | —CH(CH₃)₂ | H | H | 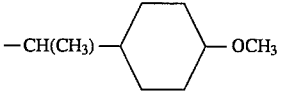 | mp.: 125° C. |
| 11 | —CH(CH₃)₂ | H | —CH(CH₃)₂ | H | H | 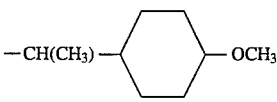 | mp.: 127° C. |
| 12 | —CH(CH₃)—CH₂CH₃ | H | —CH(CH₃)₂ | H | H | 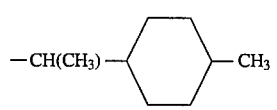 | mp.: 100° C. |
| 13 | —CH(CH₃)₂ | H | —CH(CH₃)₂ | H | H | 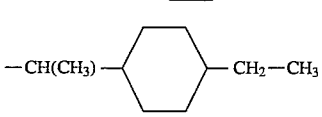 | mp.: 150° C. |
| 14 | —CH(CH₃)₂ | H | —CH(CH₃)₂ | H | H | 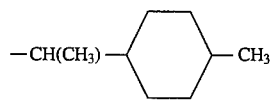 | mp.: 153° C. (R+)-amine |
| 15 | —CH(CH₃)₂ | H | —CH(CH₃)₂ | H | H | 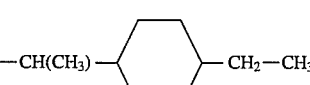 | mp.: 118° C. (R+)-amide |
| 16 | —CH(CH₃)CH₂CH₃ | H | —CH(CH₃)₂ | H | H | 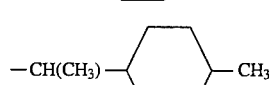 | mp.: 90° C. (R+)-amide |
| 17 | —CH(CH₃)₂ | H | —CH(CH₃)₂ | H | H |  | mp.: 115° C. (R+)-amide |
| 18 | —CH(CH₃)—CH₂CH₃ | H | —CH(CH₃)₂ | H | H | 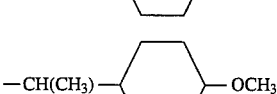 | racemate |
| 19 | —CH(CH₃)—CH₂CH₃ | H | —CH(CH₃)₂ | H | H | 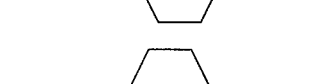 | racemate (R+)-amine |
| 20 | —CH(CH₃)—CH₂CH₃ | H | —CH(CH₃)₂ | H | H | 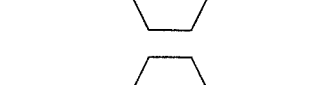 | (R+)-amide |

EXAMPLE A

Phytophthora test (tomato)/protective

Solvent: 4,7 parts by weight of acetone

Emulsifier: 0,3 parts by weight of alkyl-arylpolyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are placed in an incubation cabin at 100% relative atmospheric humidity and at about 20° C.

Evaluation is carried out 3 days after the inoculation.

In this test, a clearly superior activity compared with the prior art is shown, for example, by the compounds according to the following preparation examples: 1, 7, 12, 13, 14.

We claim:

1. Amino acid amide derivatives of the general formula

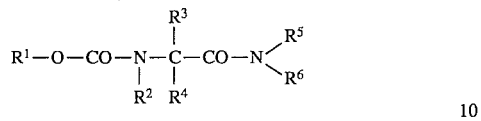

in which

R¹ represents alkyl, alkenyl, alkinyl, halogenoalkyl, halogenoalkenyl, halogenoalkinyl, cycloalkyl, cycloalkenyl, unsubstituted or substituted aryl, unsubstituted or substituted aralkyl, unsubstituted or substituted heteroaryl and unsubstituted or substituted heteroarylalkyl, $R^2$, $R^5$ are identical or different and represent hydrogen or lower-alkyl, $R^3$, $R^4$ represent hydrogen, cycloalkyl or alkyl or $R^3$ and $R^4$ together with the carbon atom to which they are bonded form a cycloalkyl ring, $R^6$ represents unsubstituted or substituted straight-chain or branched cycloalkylalkyl, unsubstituted or substituted, straight-chain or branched cycloalkenyl, alkyl or alkyl-bridged cycloalkylalkyl.

2. Compounds of the formula (I), according to claim 1, in which $R^1$ represents straight-chain or branched alkyl having 1 to 6 carbon atoms, straight-chain or branched alkenyl or alkinyl having 2 to 6 carbon atoms, straight-chain or branched halogenoalkyl having 1 to 6 carbon atoms and 1 to 9 identical or different halogen atoms, straight-chain or branched halogenoalkenyl or halogenoalkinyl having 2 to 6 carbon atoms and 1 to 9 identical or different halogen atoms or substituted or unsubstituted cycloalkyl or cycloalkenyl having 3 to 7 carbon atoms, or represents in each case unsubstituted or substituted phenyl and pyridyl, or phenylalkyl which has 1 to 4 carbon atoms in the straight-chain or branched alkyl moiety and which is unsubstituted or substituted in the phenyl moiety, suitable substituents in the pyridyl or phenyl moiety in each case being: alkyl, alkoxy and alkylthio, in each case having 1 to 4 carbon atoms; halogenoalkyl, halogenoalkoxy and halogenoalkylthio, in each case having 1 to 4 carbon atoms and 1 to 9 halogen atoms, the halogen atoms being identical or different; halogen; alkylalkoxy having 1 to 4 carbon atoms in each alkyl moiety; carbonylalkoxy having 1 to 4 carbon atoms in the alkyl moiety;

$R^2$ and $R^5$ represent hydrogen or methyl, $R^3$ and $R^4$ are identical or different and represent hydrogen, unsubstituted or substituted cycloalkyl having 3 to 7 carbon atoms or straight-chain or branched alkyl having 1 to 6 carbon atoms, or $R^3$ and $R^4$ together with the carbon atom to which they are bonded form a cycloalkyl ring having 3 to 7 carbon atoms, and $R^6$ represents unsubstituted or substituted cycloalkylalkyl having 3 to 7 carbon atoms in the cycloalkyl moiety and 1 to 6 carbon atoms in the straight-chain or branched alkyl moiety, or represents unsubstituted or substituted cycloalkenylalkyl having 5 to 8 carbon atoms in the cycloalkenyl moiety and 1 to 6 carbon atoms in the straight-chain or branched alkyl moiety, or represents cycloalkylalkyl which has 5 to 8 carbon atoms in the cycloalkyl moiety, which is unsubstituted or substituted and which is bridged by alkyl, having 1 to 4 carbon atoms in the bridging alkyl moiety and 1 to 6 carbon atoms in the straight-chain or branched alkyl moiety, suitable substituents being: alkyl, alkoxy and alkylthio, in each case having 1 to 4 carbon atoms; halogenoalkyl, halogenoalkoxy and halogenoalkylthio, in each case having 1 to 4 carbon atoms and 1 to 9 halogen atoms, the halogen atoms being identical or different; hydroxyl; dialkylamino having 1 to 4 carbon atoms per alkyl group; alkylalkoxy having 1 to 4 carbon atoms in each alkyl moiety.

3. Compounds of the formula (I), according to claim 1, in which $R^1$ represents straight-chain or branched alkyl having 1 to 4 carbon atoms, straight-chain or branched alkenyl or alkinyl having 2 to 4 carbon atoms, straight-chain or branched halogenoalkyl having 1 to 4 carbon atoms and 1 to 5 identical or different halogen atoms, straight-chain or branched halogenoalkenyl or halogenoalkinyl having 2 to 4 carbon atoms and 1 to 5 identical or different halogen atoms or unsubstituted or substituted cycloalkyl or cycloalkenyl having 3 to 6 carbon atoms, and furthermore represents phenyl which is unsubstituted or monosubstituted to trisubstituted by identical or different substituents, suitable substituents being the following: alkyl, alkoxy and alkylthio, in each case having 1 to 4 carbon atoms; halogenoalkyl, halogenoalkoxy and halogenoalkylthio having 1 or 2 carbon atoms and 1 to 5 halogen atoms, the halogen atoms being identical or different; fluorine, chlorine, bromine and iodine; alkylalkoxy having 1 to 2 carbon atoms in each alkyl moiety; carbonylalkoxy having 1 or 2 carbon atoms in the alkyl moiety;

$R^2$ and $R^5$ represent hydrogen, $R^3$ and $R^4$ are identical or different and represent hydrogen, unsubstituted or substituted cycloalkyl having 3 to 6 carbon atoms or straight-chain or branched alkyl having 1 to 5 carbon atoms, or $R^3$ and $R^4$ together with the carbon atom to which they are bonded form a cycloalkyl ring having 3 to 6 carbon atoms and $R^6$ represents unsubstituted or substituted cycloalkylalkyl having 3 to 6 carbon atoms in the cycloalkyl moiety and 1 to 4 carbon atoms in the straight-chain or branched alkyl moiety, or represents unsubstituted or substituted cycloalkenylalkyl having 5 to 7 carbon atoms in the cycloalkenyl moiety and 1 to 4 carbon atoms in the straight-chain or branched alkyl moiety, or represents cycloalkylalkyl which has 5 to 7 carbon atoms in the cycloalkyl moiety, which is unsubstituted or substituted and which is bridged by alkyl, having 1 to 3 carbon atoms in the bridging alkyl moiety and 1 to 4 carbon atoms in the straight-chain or branched alkyl moiety, suitable substituents being: alkyl, alkoxy and alkylthio, in each case having 1 to 4 carbon atoms; halogenoalkyl, halogenoalkoxy and halogenoalkylthio having 1 to 2 carbon atoms and 1 to 5 halogen atoms, the halogen atoms being identical or different; hydroxyl; dialkylamino having 1 to 2 carbon atoms per alkyl group; alkylalkoxy having 1 to 2 carbon atoms in each alkyl moiety.

4. Compounds of the formula (I), according to claim 1, in which $R^1$ represents methyl, ethyl, n- and i-propyl, n-, i-, s- and t-butyl, fluoromethyl, fluoroethyl, fluoropropyl, chloropropyl, fluorobutyl, chlorobutyl, difluoromethyl, difluoropropyl, dichloropropyl, difluorobutyl, dichlorobutyl, trifluoromethyl, trichloromethyl, trifluoroethyl, trichloroethyl, trifluoropropyl, trichloropropyl, trifluorobutyl, trichlorobutyl, allyl, butenyl, propargyl, butinyl, fluoro or chloroallyl, -butenyl, -propargyl, -butinyl, cyclopropyl, cyclopentyl, cyclohexyl, cyclopentenyl, cyclohexenyl, or represents phenyl which is unsubstituted or monosubstituted to disubstituted by identical or different substituents, suitable substituents being the following: methyl, ethyl, n- and i-propyl, n-, i-, s- and t-butyl, methoxy, ethoxy, i- and n-propoxy, n-, i-, s- and t-butoxy, trifluoromethyl, difluoromethyl, pentafluoroethyl, tetrafluoroethyl, trifluorochloroethyl, trifluoroethyl, trifluoroethoxy, difluoromethoxy, pentafluoroethoxy, tetrafluoroethoxy, trifluorochloroethoxy, trifluoromethoxy and trifluoromethylthio; chlorine, bromine, fluorine, and $R^2$ and $R^5$ represent hydrogen and $R^3$ and $R^4$ are identical or different and represent hydrogen, methyl, ethyl, n- or i-propyl, n-, i-, s- or t-butyl, 3-pentyl, cyclopropyl, cyclopentyl or cyclohexyl or $R^3$ and $R^4$ together with the carbon atom to which they are bonded form a cyclopropyl, cyclopentyl or cyclohexyl ring, $R^6$ represents unsubstituted or substituted cycloalkylalkyl having 3, 5 or 6 carbon atoms in the cycloalkyl moiety and 1 to 3 carbon atoms in the straight-chain or branched alkyl moiety, or represents unsubstituted or substituted cycloalkenylalkyl having 5 to 7 carbon atoms in the cycloalkenyl moiety and 1 to 3 carbon atoms in the straight-chain or branched alkyl moiety, or represents unsubstituted or substituted cycloalkylalkyl which is bridged by alkyl and which has 5 to 7 carbon atoms in the cycloalkyl moiety, having 1 to 2 carbon atoms in the bridging alkyl moiety and 1 to 3 carbon atoms in the straight-chain or branched alkyl moiety, suitable substituents being the following: methyl, ethyl, n- and i-propyl, n-, i-, s- and t-butyl, methoxy, ethoxy, i-and n-propoxy, n-, i-, s- and t-butoxy, trifluormethyl, difluoromethyl, pentafluoroethyl, tetrafluoroethyl, trifluorochloroethyl, trifluoroethyl, trifluoroethoxy, difluoromethoxy, pentafluoroethoxy, tetrafluoroethoxy, trifluorochloroethoxy, trifluoromethoxy and trifluoromethylthio, hydroxyl, methylthio, ethylthio, n- and i-propylthio, dimethylamino, diethylamino.

5. A method of combating fungi which comprises applying to such fungi or to a locus from which it is desired to exclude such fungi a fungicidally effective amount of a compound according to claim 1.

6. The method according to claim 5, in which $R^1$ represents straight-chain or branched alkyl having 1 to 6 carbon atoms, straight-chain or branched alkenyl or alkinyl having 2 to 6 carbon atoms, straight-chain or branched halogenoalkyl having 1 to 6 carbon atoms and 1 to 9 identical or different halogen atoms, straight-chain or branched halogenoalkenyl or halogenoalkinyl having 2 to 6 carbon atoms and 1 to 9 identical or different halogen atoms, or substituted or unsubstituted cycloalkyl or cycloalkenyl having 3 to 7 carbon atoms, or represents in each case unsubstituted or substituted phenyl and pyridyl, or phenylalkyl which has 1 to 4 carbon atoms in the straight-chain or branched alkyl moiety and which is unsubstituted or substituted in the phenyl moiety, substituents in the pyridyl, or phenyl moiety in each case being selected from the group consisting of alkyl, alkoxy and alkylthio, in each case having 1 to 4 carbon atoms; halogenoalkyl, halogenoalkoxy and halogenoalkylthio, in each case having 1 to 4 carbon atoms and 1 to 9 halogen atoms, the halogen atoms being identical or different; halogen; alkylalkoxy having 1 to 4 carbon atoms in each alkyl moiety; and carbonylalkoxy having 1 to 4 carbon atoms in the alkyl moiety;

$R^2$ and $R^5$ represent hydrogen or methyl, $R^3$ and $R^4$ are identical or different and represent hydrogen, unsubstituted or substituted cycloalkyl having 3 to 7 carbon atoms or straight-chain or branched alkyl having 1 to 6 carbon atoms, or $R^3$ and $R^4$ together with the carbon atom to which they are bonded form a cycloalkyl ring having 3 to 7 carbon atoms, and $R^6$ represents unsubstituted or substituted cycloalkylalkyl having 3 to 7 carbon atoms in the cycloalkyl moiety and 1 to 6 carbon atoms in the straight-chain or branched alkyl moiety, or represents unsubstituted or substituted cycloalkenylalkyl having 5 to 8 carbon atoms in the cycloalkenyl moiety and 1 to 6 carbon atoms in the straight-chain or branched alkyl moiety, or represents cycloalkylalkyl which has 5 to 8 carbon atoms in the cycloalkyl moiety, which is unsubstituted or substituted and which is bridged by alkyl, having 1 to 4 carbon atoms in the bridging alkyl moiety and 1 to 6 carbon atoms in the straight-chain or branched alkyl moiety, substituents being selected from the group consisting of alkyl, alkoxy and alkylthio, in each case having 1 to 4 carbon atoms; halogenoalkyl, halogenoalkoxy and halogenoalkylthio, in each case having 1 to 4 carbon atoms and 1 to 9 halogen atoms, the halogen atoms being identical or different; hydroxyl; dialkylamino having 1 to 4 carbon atoms per alkyl group; and alkylalkoxy having 1 to 4 carbon atoms in each alkyl moiety.

7. The method according to claim 5, in which $R^1$ represents straight-chain or branched alkyl having 1 to 4 carbon atoms, straight-chain or branched alkenyl or alkinyl having 2 to 4 carbon atoms, straight-chain or branched halogenoalkyl having 1 to 4 carbon atoms and 1 to 5 identical or different halogen atoms, straight-chain or branched halogenoalkenyl or halogenoalkinyl having 2 to 4 carbon atoms and 1 to 5 identical or different halogen atoms, or unsubstituted or substituted cycloalkyl or cycloalkenyl having 3 to 6 carbon atoms, and furthermore represents phenyl which is unsubstituted or monosubstituted to trisubstituted by identical or different substituents selected from the group consisting of alkyl, alkoxy and alkylthio, in each case having 1 to 4 carbon atoms; halogenoalkyl, halogenoalkoxy and halogenoalkylthio having 1 or 2 carbon atoms and 1 to 5 halogen atoms, the halogen atoms being identical or different; fluorine, chlorine, bromine and iodine; alkylalkoxy having 1 to 2 carbon atoms in each alkyl moiety; and carbonylalkoxy having 1 or 2 carbon atoms in the alkyl moiety;

$R^2$ and $R^5$ represent hydrogen, $R^3$ and $R^4$ are identical or different and represent hydrogen, unsubstituted or substituted cycloalkyl having 3 to 6 carbon atoms or straight-chain or branched alkyl having 1 to 5 carbon atoms, or $R^3$ and $R^4$ together with the carbon atom to which they are bonded form a cycloalkyl ring having 3 to 6 carbon atoms and $R^6$ represents unsubstituted or substituted cycloalkylalkyl having 3 to 6 carbon atoms in the cycloalkyl moiety and 1 to 4 carbon atoms in the straight-chain or branched alkyl moiety, or represents unsubstituted or substituted cycloalkenylalkyl having 5 to 7 carbon atoms in the cycloalkenyl moiety and 1 to 4 carbon atoms in the straight-chain or branched alkyl moiety, or represents cycloalkylalkyl which has 5 to 7 carbon atoms in the cycloalkyl moiety, which is unsubstituted or substituted and which is bridged by alkyl having 1 to 3 carbon atoms in the bridging alkyl moiety and 1 to 4 carbon atoms in the straight-chain or branched alkyl moiety, substituents being selected from the group consisting of alkyl, alkoxy and alkylthio, in each case having 1 to 4 carbon atoms; halogenoalkyl, halogenoalkoxy and halogenoalkylthio having 1 to 2 carbon atoms and 1 to 5 halogen atoms, the halogen atoms being identical or different; hydroxyl; dialkylamino having 1 to 2 carbon atoms per alkyl group; and alkylalkoxy having 1 to 2 carbon atoms in each alkyl moiety.

8. The method according to claim 5, in which $R^1$ represents methyl, ethyl, n- and i-propyl, n-, i-, s- and t-butyl, fluoromethyl, fluoroethyl, fluoropropyl, chloropropyl, fluorobutyl, chlorobutyl, difluoromethyl, difluoropropyl, dichloropropyl, difluorobutyl, dichlorobutyl, trifluoromethyl, trichtoromethyl, trifluoroethyl, trichloroethyl, trifluoropropyl, trichloropropyl, trifluorobutyl, trichlorobutyl, allyl, butenyl, propargyl, butinyl, fluoro or chloroallyl, butenyl, propargyl or butinyl, cyclopropyl, cyclopentyl, cyclohexyl, cyclopentenyl or cyclohexenyl, or represents phenyl which is unsubstituted or monosubstituted to disubstituted by identical or different substituents selected from the group consisting of methyl, ethyl, n- and i-propyl, n-, i-, s- and t-butyl, methoxy, ethoxy, i- and n-propoxy, n-, i-, s- and t-butoxy, trifluoromethyl, difluoromethyl, pentafluoroethyl, tetrafluoroethyl, trifluorochloroethyl, trifluoroethyl, trifluoroethoxy, difluoromethoxy, pentafluoroethoxy, tetrafluoroethoxy, trifluorochloroethoxy, trifluoromethoxy and trifluoromethylthio; chlorine, bromine and fluorine, and $R^2$ and $R^5$ represent hydrogen and $R^3$ and $R^4$ are identical or different and represent hydrogen, methyl, ethyl, n- or i-propyl, n-, i-, s- or t-butyl, 3-pentyl, cyclopropyl, cyclopentyl or cyclohexyl or $R^3$ and $R^4$ together with the carbon atom to which they are bonded form a cyclopropyl, cyclopentyl or cyclohexyl ring, $R^6$ represents unsubstituted or substituted cycloalkylalkyl having 3, 5 or 6 carbon atoms in the cycloalkyl moiety and 1 to 3 carbon atoms in the straight-chain or branched alkyl moiety, or represents unsubstituted or substituted cycloalkenylalkyl having 5 to 7 carbon atoms in the cycloalkenyl moiety and 1 to 3 carbon atoms in the straight-chain or branched alkyl moiety, or represents unsubstituted or substituted cycloalkylalkyl which is bridged by alkyl and which has 5 to 7 carbon atoms in the cycloalkyl moiety, having 1 to 2 carbon atoms in the bridging alkyl moiety and 1 to 3 carbon atoms in the straight-chain or branched alkyl moiety, substituents being selected from the group consisting of methyl, ethyl, n- and i-propyl, n-, i-, s- and t-butyl, methoxy, ethoxy, i- and n-propoxy, n-, i-, s- and t-butoxy, trifluormethyl, difluoromethyl, pentafluoroethyl, tetrafluoroethyl, trifluorochloroethyl, trifluoroethyl, trifluoroethoxy, difluoromethoxy, pentafluoroethoxy, tetrafluoroethoxy, trifluorochloroethoxy, trifluoromethoxy, trifluoromethylthio, hydroxyl, methylthio, ethylthio, n- and i-propylthio, dimethylamino and diethylamino.

9. The method according to claim 5, wherein such compound is $N^2$-isopropyloxycarbonyl-N'(1-cyclohexylethyl)-valinamide of the formula

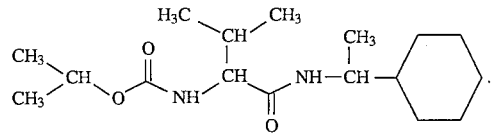

10. A pesticidal composition comprising a pesticidally-effective amount of at least one amino-acid derivative according to claim 1 and a solvent or a solid carrier.

* * * * *

UNITED STATES PATENT AND TRADEMARK OFFICE
CERTIFICATE OF CORRECTION

PATENT NO.  : 5,504,109
DATED       : April 2, 1996
INVENTOR(S) : Seitz, et al.

It is certified that error appears in the above-indentified patent and that said Letters Patent is hereby corrected as shown below:

Column 19, line 26, delete "trichtoromethyl" and substitute --trichloromethyl--.

Signed and Sealed this

Twenty-fourth Day of December, 1996

Attest:

BRUCE LEHMAN

*Attesting Officer*      *Commissioner of Patents and Trademarks*